US00PP23460P2

(12) United States Plant Patent
Hooper

(10) Patent No.: US PP23,460 P2
(45) Date of Patent: Mar. 12, 2013

(54) ***CORNUS* PLANT NAMED 'GOLDEN WEDDING'**

(50) Latin Name: *Cornus contraversa*
Varietal Denomination: Golden Wedding

(76) Inventor: Vance James Hooper, Waitara (NZ)

( * ) Notice: Subject to any disclaimer, the term of this patent is extended or adjusted under 35 U.S.C. 154(b) by 0 days.

(21) Appl. No.: 13/136,390

(22) Filed: Jul. 29, 2011

(51) Int. Cl.
*A01H 5/00* (2006.01)
(52) U.S. Cl. ..... Plt./220
(58) Field of Classification Search ..... Plt./220
See application file for complete search history.

*Primary Examiner* — Annette Para
(74) *Attorney, Agent, or Firm* — Mark P. Bourgeois

(57) ABSTRACT

A new cultivar of *Cornus* plant named 'Golden Wedding' that is characterized by ovate shaped leaves with a green center and golden margins and lateral branches that radiate outward and slightly downward.

1 Drawing Sheet

Botanical classification: *Cornus contraversa.*
Variety denomination: 'Golden Wedding'.

BACKGROUND OF THE INVENTION

The present invention relates to a new and distinct cultivar of *Cornus* plant botanically known as *Cornus contraversa* and hereinafter referred to by the cultivar name 'Golden Wedding'.

'Golden Wedding' was discovered as a naturally occurring branch mutation of *Cornus contraversa* 'Variegata' (not patented). The cultivar 'Golden Wedding' was discovered by the inventor in 2005 in a cultivated area of Waitara, New Zealand.

Asexual reproduction of the new cultivar 'Golden Wedding' by field budding was first performed in 2007 in Waitara, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Cornus* cultivar 'Golden Wedding'. These traits in combination distinguish 'Golden Wedding' as a new and distinct cultivar.

1. *Cornus* 'Golden Wedding' exhibits leaves with a green center and golden margins.
2. *Cornus* 'Golden Wedding' exhibits lateral branches that radiate outward and slightly downward.
3. *Cornus* 'Golden Wedding' exhibits ovate shaped leaves.

The closest comparison cultivar is the parent plant *Cornus* 'Variegata'. 'Golden Wedding' is different than 'Variegata' in the following characteristics:

1. 'Golden Wedding' has ovate shaped leaves. The leaves of 'Variegata' are elliptic in shape.
2. 'Golden Wedding' has leaves with a green center and golden margins. The leaves of 'Variegata' have cream colored margins.
3. 'Golden Wedding' has lateral branches that radiate outward and slightly downward. The lateral branches of 'Variegata' extend outward and upward.

BRIEF DESCRIPTION OF THE DRAWING

The accompanying photograph illustrates the distinguishing traits of *Cornus* 'Golden Wedding'. The plant in the photograph shows an overall view of a 3 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Cornus* cultivar named 'Golden Wedding'. Data was collected in Waitara, New Zealand from 2 year old field grown plants. The time of year was Autumn in the Southern Hemisphere and the average temperature was 18 to 25° Centigrade during the day and 6 to 12° Centigrade at night. Color determinations are in accordance with The Royal Horticultural Society Colour Chart 2001 edition, except where general color terms of ordinary dictionary significance are used. The growing requirements are similar to the species. 'Golden Wedding' has not been tested under all possible conditions and phenotypic differences may be observed with variations in environmental, climatic, and cultural conditions, however, without any variance in genotype.

Botanical classification: *Cornus contraversa* 'Golden Wedding'.
Use: Ornamental Tree.
Parentage: 'Golden Wedding' is a naturally occurring branch mutation of *Cornus contraversa* 'Variegata'.
Vigor: Strong.
Growth habit: Upright.
Plant shape: Triangular shape with tiers of foliage.
Height: Average 2.1 m. in height.
Width: Average 1.3 m. in width.
Hardiness: −18° to 40° C.
Propagation: Softwood cuttings and field budding.
Crop time: 2 years.
Stem:
*Branching habit.*—Lateral branches extend outward and slightly downward.
*Number of lateral branches.*—25 to 35.
*Lateral branch diameter.*—7 to 10 mm. in diameter.
*Lateral branch length.*—20 to 50 cm. in length.
*Lateral branch strength.*—Moderately strong.
*Stem color.*—197C.

*Pubescence*.—Short hairs present on young branches.
*Internode length*.—5 to 10 cm. between nodes.
*Shape*.—Round.
*Surface*.—Smooth.
*Stem strength*.—Moderately strong.
*Lenticles*.—2.0 mm. in length, 1.0 mm. in width, color 156C.

Foliage:

*Leaf arrangement*.—Opposite.
*Compound or single*.—Single.
*Quantity of leaves per lateral branch*.—30 to 40.
*Leaf shape*.—Ovate.
*Leaf apex*.—Acuminate.
*Leaf base*.—Cuneate.
*Leaf length*.—14 cm. in length.
*Leaf width*.—8 cm. in width.
*Texture*.—Smooth.
*Pubescence*.—Absent.
*Leaf margin*.—Entire.
*Vein pattern*.—Pinnate.
*Young leaf color* (*upper surface*).—141A with margins 14D.
*Young leaf color* (*lower surface*).—141A with margins 14D.
*Mature leaf color* (*upper surface*).—141A with margins 14D.
*Mature leaf color* (*lower surface*).—141A with margins 14D.
*Leaf attachment*.—Petiolate.
*Petiole dimensions*.—3.5 cm. in length, 4 mm. in width.
*Petiole color*.—144B.
*Durability of foliage to stress*.—High.

Flowers: 'Golden Wedding' does not produce flowers.

Disease and pest resistance: Plants of the new *Cornus* have not been observed for disease or pest resistance.

What is claimed is:

1. A new and distinct variety of *Cornus* plant named 'Golden Wedding' as described and illustrated.

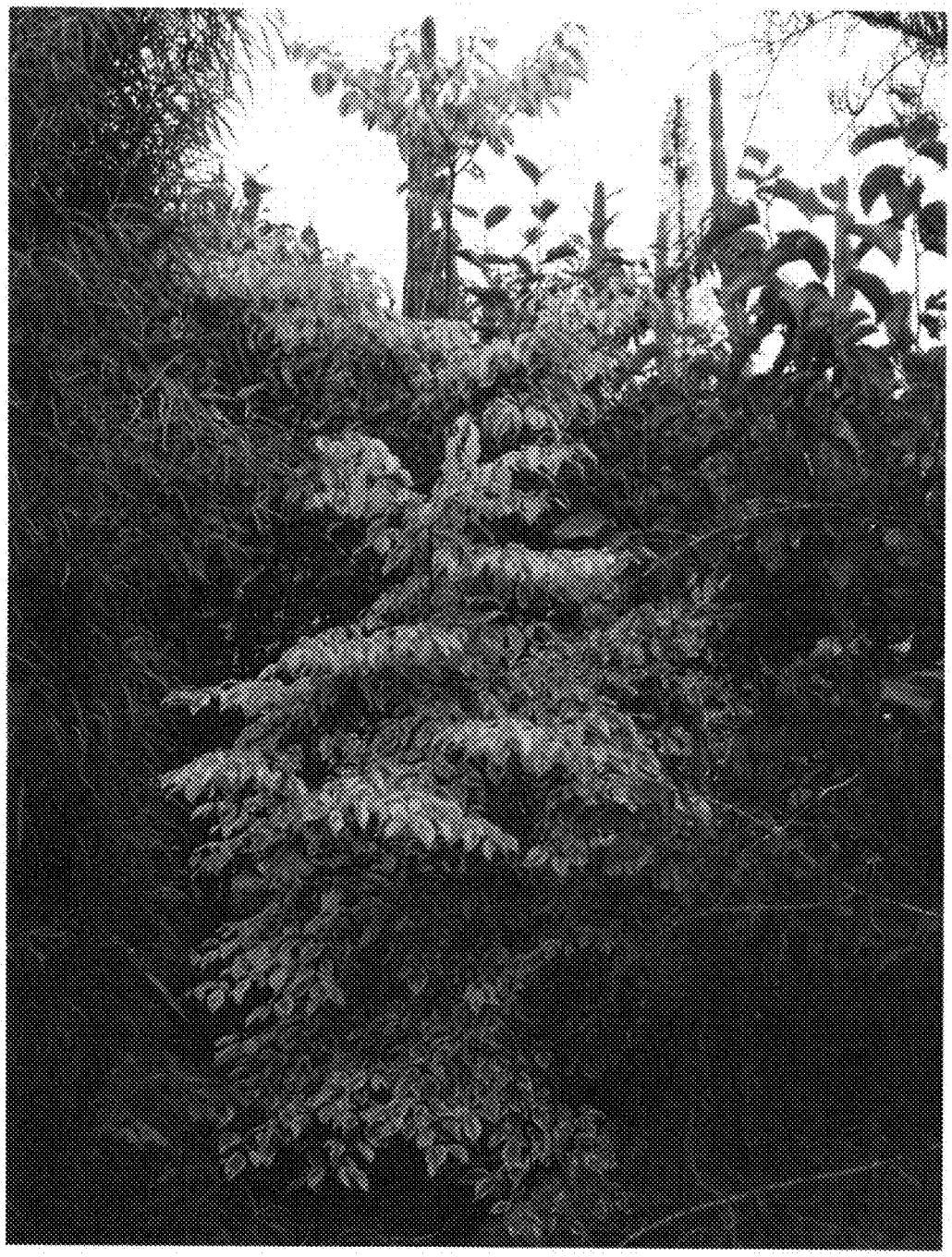

* * * * *